(12) United States Patent
Euteneuer et al.

(10) Patent No.: US 7,824,345 B2
(45) Date of Patent: Nov. 2, 2010

(54) MEDICAL DEVICE WITH PUSH FORCE LIMITER

(75) Inventors: Charles L. Euteneuer, St. Michael, MN (US); Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 729 days.

(21) Appl. No.: 10/746,220

(22) Filed: Dec. 22, 2003

(65) Prior Publication Data

US 2005/0137501 A1 Jun. 23, 2005

(51) Int. Cl.
*A61M 25/00* (2006.01)
*A61M 5/178* (2006.01)
*A61M 25/098* (2006.01)

(52) U.S. Cl. .................. 600/585; 600/433; 600/434; 600/435; 604/164.13; 604/264; 604/523; 604/524; 604/525; 604/529

(58) Field of Classification Search ......... 600/433–435, 600/585, 564, 566, 567, 568; 604/164.13, 604/264, 523–525, 529; 606/29, 31, 35, 606/41, 42, 45, 48, 49, 50, 167, 170; 607/98, 607/99, 100, 101, 102, 124
See application file for complete search history.

(56) References Cited

U.S. PATENT DOCUMENTS

| 1,553,227 | A | 9/1925 | Feyk et al. |
|---|---|---|---|
| 1,866,888 | A | 7/1932 | Hawley |
| 2,275,827 | A | 3/1942 | Plensler |
| 2,413,805 | A | 1/1947 | Vickers |
| 2,441,166 | A | 5/1948 | Raspert |
| 2,561,890 | A | 7/1951 | Stoddard |
| 2,722,614 | A | 11/1955 | Fryklund |
| 2,857,536 | A | 10/1958 | Light |
| 2,864,017 | A | 12/1958 | Waltscheff |
| 2,871,793 | A | 2/1959 | Michie et al. |
| 3,249,776 | A | 5/1966 | Anderson et al. |
| 3,322,984 | A | 5/1967 | Anderson |
| 3,334,253 | A | 8/1967 | Hill |
| 3,363,470 | A | 1/1968 | Yavne |
| 3,452,227 | A | 6/1969 | Welch |
| 3,452,742 | A | 7/1969 | Muller |
| 3,463,953 | A | 8/1969 | Maxwell |
| 3,512,019 | A | 5/1970 | Durand |

(Continued)

FOREIGN PATENT DOCUMENTS

AU    723040    12/1997

(Continued)

OTHER PUBLICATIONS

"Mechanical Design and Systems Handbook", H.A. Rothbart, 1964, p. 33-13 (one sheet).

*Primary Examiner*—Max Hindenburg
*Assistant Examiner*—Jeffrey G Hoekstra
(74) *Attorney, Agent, or Firm*—Crompton, Seager & Tufte, LLC (57) ABSTRACT

A medical device with improved flexibility characteristics and methods of using the same. The medical device may include a proximal end, a distal end, and an intermediate region. In at least some embodiments, the column strength or flexibility of the intermediate portion is generally greater than the column strength or flexibility at the distal end.

37 Claims, 5 Drawing Sheets

U.S. PATENT DOCUMENTS

| | | |
|---|---|---|
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,050,466 A | 9/1977 | Koerbacher |
| 4,142,119 A | 2/1979 | Madey |
| 4,215,703 A | 8/1980 | Willson |
| 4,280,500 A | 7/1981 | Ono |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Towne et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,213,111 A | 5/1993 | Cook et al. |
| 5,228,441 A | 7/1993 | Lundquist |
| 5,228,453 A | 7/1993 | Sepetka |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,314,418 A | 5/1994 | Takano et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,433,200 A | 7/1995 | Fleischhacker, Jr. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |

| Patent No. | Date | Inventor(s) |
|---|---|---|
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirazee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,891,056 A * | 4/1999 | Ramzipoor .................. 600/585 |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A * | 6/1999 | Berg et al. .................. 604/525 |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,819 A | 8/1999 | Fariabi |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 5,980,471 A | 11/1999 | Jafari |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,113,557 A | 9/2000 | Fagan et al. |
| 6,120,516 A | 9/2000 | Selmon et al. |
| 6,139,510 A | 10/2000 | Palermo |
| 6,139,543 A | 10/2000 | Esch et al. |
| 6,165,292 A | 12/2000 | Abrams et al. |
| 6,171,296 B1 | 1/2001 | Chow |
| 6,183,410 B1 | 2/2001 | Jacobsen et al. |
| 6,183,420 B1 | 2/2001 | Duek et al. |
| 6,193,686 B1 | 2/2001 | Estrada et al. |
| 6,197,014 B1 | 3/2001 | Samson et al. |
| 6,203,485 B1 | 3/2001 | Urick et al. |
| RE37,148 E | 4/2001 | Shank |
| 6,210,400 B1 | 4/2001 | Hebert et al. |
| 6,214,042 B1 | 4/2001 | Jacobsen et al. |
| 6,217,527 B1 | 4/2001 | Selmon et al. |
| 6,221,049 B1 | 4/2001 | Selmon et al. |
| 6,228,073 B1 | 5/2001 | Noone et al. |
| 6,231,546 B1 | 5/2001 | Milo et al. |
| 6,235,000 B1 | 5/2001 | Milo et al. |
| 6,241,744 B1 | 6/2001 | Imran et al. |
| 6,248,082 B1 | 6/2001 | Jafari |
| 6,251,092 B1 | 6/2001 | Qin et al. |
| 6,254,469 B1 | 7/2001 | Angell et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,306,105 B1 | 10/2001 | Rooney et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,402,706 B2 | 6/2002 | Richardson et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen et al. |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,506,178 B1 | 1/2003 | Schubart et al. |
| 6,508,803 B1 | 1/2003 | Horikawa et al. |
| 6,511,458 B2 | 1/2003 | Milo et al. |
| 6,524,301 B1 | 2/2003 | Wilson et al. |

| | | | | | | |
|---|---|---|---|---|---|---|
| 6,527,732 | B1 | 3/2003 | Strauss et al. | 2008/0077119 A1 | 3/2008 | Snyder et al. |
| 6,530,934 | B1 | 3/2003 | Jacobsen et al. | | | |
| 6,547,779 | B2 | 4/2003 | Levine et al. | FOREIGN PATENT DOCUMENTS | | |
| 6,553,880 | B2 | 4/2003 | Jacobsen et al. | | | |
| 6,556,873 | B1 | 4/2003 | Smits | AU | 733966 | 4/1998 |
| 6,579,246 | B2 | 6/2003 | Jacobsen et al. | BR | PI 9712829 | 1/2000 |
| 6,579,302 | B2 | 6/2003 | Duerig et al. | CA | 2266685 | 5/2006 |
| 6,602,207 | B1 | 8/2003 | Mann et al. | CA | 2255781 | 3/2007 |
| 6,602,280 | B2 | 8/2003 | Chobotov | CN | 1230914 | 10/1999 |
| 6,610,046 | B1 | 8/2003 | Usami et al. | DE | 2539191 | 3/1976 |
| 6,623,448 | B2 | 9/2003 | Slater | DE | 285514 | 12/1990 |
| 6,636,758 | B2 | 10/2003 | Sanchez et al. | EP | 0 045 931 | 2/1982 |
| 6,638,266 | B2 | 10/2003 | Wilson et al. | EP | 0 069 522 | 1/1983 |
| 6,652,508 | B2 | 11/2003 | Griffin et al. | EP | 0 087 933 | 9/1983 |
| 6,682,493 | B2 | 1/2004 | Mirigian | EP | 0 111 044 | 6/1984 |
| 6,689,120 | B1 | 2/2004 | Gerdts | EP | 0 181 174 | 5/1986 |
| 6,702,762 | B2 | 3/2004 | Jafari et al. | EP | 0377453 | 7/1990 |
| 6,712,826 | B2 | 3/2004 | Lui | EP | 0 565 065 | 6/1996 |
| 6,730,095 | B2 | 5/2004 | Olson, Jr. et al. | EP | 0 778 038 | 6/1997 |
| 6,749,560 | B1 | 6/2004 | Konstorum et al. | EP | 0 778 039 | 6/1997 |
| 6,766,720 | B1 | 7/2004 | Jacobsen et al. | EP | 0 778 040 | 6/1997 |
| 6,777,644 | B2 | 8/2004 | Peacock, III et al. | EP | 0 812 599 | 12/1997 |
| 6,811,544 | B2 | 11/2004 | Schaer | EP | 0 865 772 | 9/1998 |
| 6,837,898 | B2 | 1/2005 | Boyle et al. | EP | 0 865 773 | 9/1998 |
| 6,866,642 | B2 | 3/2005 | Kellerman et al. | EP | 0 917 885 | 5/1999 |
| 6,887,235 | B2 | 5/2005 | O'Connor et al. | EP | 0521595 | 5/1999 |
| 6,918,882 | B2 | 7/2005 | Skujins et al. | EP | 0 937 481 | 8/1999 |
| 6,997,937 | B2 | 2/2006 | Jacobsen et al. | EP | 0 790 066 | 4/2000 |
| 7,001,369 | B2 | 2/2006 | Griffin et al. | EP | 0608853 | 4/2003 |
| 7,074,197 | B2 | 7/2006 | Reynolds et al. | EP | 0 935 947 | 12/2004 |
| 7,153,277 | B2 | 12/2006 | Skujins et al. | EP | 0 934 141 | 11/2005 |
| 7,169,118 | B2 | 1/2007 | Reynolds et al. | GB | 03531 | 7/1913 |
| 7,182,735 | B2 | 2/2007 | Shireman et al. | GB | 2214354 | 8/1989 |
| 2001/0009980 | A1* | 7/2001 | Richardson et al. ......... 600/585 | GB | 2257269 | 1/1993 |
| 2001/0012924 | A1 | 8/2001 | Milo et al. | JP | 58-8522 | 1/1983 |
| 2002/0013540 | A1 | 1/2002 | Jacobsen et al. | JP | 60091858 | 5/1985 |
| 2002/0019599 | A1 | 2/2002 | Rooney et al. | JP | 61022752 | 1/1986 |
| 2002/0082524 | A1 | 6/2002 | Anderson et al. | JP | 62023361 | 1/1987 |
| 2002/0128677 | A1 | 9/2002 | Duerig et al. | JP | 62089470 | 4/1987 |
| 2003/0009208 | A1 | 1/2003 | Snyder et al. | JP | 62299277 | 12/1987 |
| 2003/0023261 | A1 | 1/2003 | Tomaschko et al. | JP | 6393516 | 4/1988 |
| 2003/0060732 | A1 | 3/2003 | Jacobsen et al. | JP | 63-181774 | 7/1988 |
| 2003/0065316 | A1 | 4/2003 | Levine et al. | JP | 63217966 | 9/1988 |
| 2003/0069520 | A1 | 4/2003 | Skujins et al. | JP | 1089956 | 4/1989 |
| 2003/0069521 | A1 | 4/2003 | Reynolds et al. | JP | 1135363 | 5/1989 |
| 2003/0069522 | A1 | 4/2003 | Jacobsen et al. | JP | 1158936 | 6/1989 |
| 2003/0083643 | A1 | 5/2003 | Wilson et al. | JP | 2107268 | 4/1990 |
| 2003/0139763 | A1 | 7/2003 | Duerig et al. | JP | 3081831 | 4/1991 |
| 2003/0216668 | A1 | 11/2003 | Howland et al. | JP | 03-122850 | 12/1991 |
| 2004/0116831 | A1 | 6/2004 | Vrba | JP | 4061840 | 2/1992 |
| 2004/0142643 | A1 | 7/2004 | Miller et al. | JP | 4099963 | 3/1992 |
| 2004/0167437 | A1* | 8/2004 | Sharrow et al. ............ 600/585 | JP | 4213069 | 8/1992 |
| 2004/0167441 | A1 | 8/2004 | Reynolds et al. | JP | 4213070 | 8/1992 |
| 2004/0181174 | A2 | 9/2004 | Davis et al. | JP | 4236965 | 8/1992 |
| 2004/0181176 | A1 | 9/2004 | Jafari et al. | JP | 5149969 | 6/1993 |
| 2004/0243102 | A1 | 12/2004 | Berg et al. | JP | 5-506806 | 10/1993 |
| 2006/0121218 | A1 | 6/2006 | Obara et al. | JP | 5-309159 | 11/1993 |
| 2006/0122537 | A1 | 6/2006 | Reynolds et al. | JP | 5-507857 | 11/1993 |
| 2006/0189896 | A1 | 8/2006 | Davis et al. | JP | 6-501179 | 2/1994 |
| 2006/0264904 | A1 | 11/2006 | Kerby et al. | JP | 631749 | 4/1994 |
| 2008/0021347 | A1 | 1/2008 | Jacobsen et al. | JP | 6169996 | 6/1994 |
| 2008/0021348 | A1 | 1/2008 | Jacobsen et al. | JP | 6-63224 | 9/1994 |
| 2008/0021400 | A1 | 1/2008 | Jacobsen et al. | JP | 6312313 | 11/1994 |
| 2008/0021401 | A1 | 1/2008 | Jacobsen et al. | JP | 728562 | 5/1995 |
| 2008/0021402 | A1 | 1/2008 | Jacobsen et al. | JP | 7124164 | 5/1995 |
| 2008/0021403 | A1 | 1/2008 | Jacobsen et al. | JP | 7124263 | 5/1995 |
| 2008/0021404 | A1 | 1/2008 | Jacobsen et al. | JP | 7136280 | 5/1995 |
| 2008/0021405 | A1 | 1/2008 | Jacobsen et al. | JP | 7148264 | 6/1995 |
| 2008/0021406 | A1 | 1/2008 | Jacobsen et al. | JP | 7505561 | 6/1995 |
| 2008/0021407 | A1 | 1/2008 | Jacobsen et al. | JP | 7037199 | 7/1995 |
| 2008/0021408 | A1 | 1/2008 | Jacobsen et al. | JP | 7185009 | 7/1995 |
| | | | | JP | 7255855 | 10/1995 |
| | | | | JP | 7275366 | 10/1995 |

| | | | | | | |
|---|---|---|---|---|---|---|
| JP | 751067 | 11/1995 | | WO | WO 95/24236 | 9/1995 |
| JP | 8-229888 | 9/1996 | | WO | WO 96/19255 | 6/1996 |
| JP | 8509141 | 10/1996 | | WO | WO 97/10022 | 3/1997 |
| JP | 8-317988 | 12/1996 | | WO | WO 97/25914 | 7/1997 |
| JP | 9000164 | 4/1997 | | WO | WO 97/43949 | 11/1997 |
| JP | 9-276413 | 10/1997 | | WO | WO 97/44083 | 11/1997 |
| JP | 9-294813 A | 11/1997 | | WO | WO 97/44086 | 11/1997 |
| JP | 10-118193 | 5/1998 | | WO | WO 98/10694 | 3/1998 |
| JP | 10328191 | 12/1998 | | WO | WO 99/04847 | 2/1999 |
| JP | 11-267224 A | 10/1999 | | WO | WO 99/11313 | 3/1999 |
| JP | 2000-197704 A | 7/2000 | | WO | WO 00/27303 | 5/2000 |
| JP | 2000-510722 A | 8/2000 | | WO | WO 00/30710 | 6/2000 |
| JP | 2000-511083 A | 8/2000 | | WO | WO 00/48645 | 8/2000 |
| JP | 2001-500808 A | 1/2001 | | WO | WO 00/57943 | 10/2000 |
| JP | 3325828 | 7/2002 | | WO | WO 00/66199 | 11/2000 |
| JP | 2002-529137 A | 9/2002 | | WO | WO 00/67845 | 11/2000 |
| JP | 2002-542901 A | 12/2002 | | WO | WO 00/72907 | 12/2000 |
| JP | 2002-543896 A | 12/2002 | | WO | WO 01/28620 | 4/2001 |
| JP | 2003-517893 A | 6/2003 | | WO | WO 01/36034 | 5/2001 |
| JP | 3649604 | 2/2005 | | WO | WO 01/45773 | 6/2001 |
| JP | 2005-534407 | 11/2005 | | WO | WO 01/45912 | 6/2001 |
| SU | 712908 | 1/1980 | | WO | WO 01/93920 | 12/2001 |
| SU | 758421 | 8/1980 | | WO | WO 02/013682 | 2/2002 |
| SU | 1529365 | 12/1989 | | WO | 02062540 | 8/2002 |
| WO | 9002520 | 3/1990 | | WO | WO 03/004086 | 1/2003 |
| WO | WO 91/13364 | 9/1991 | | WO | WO 03/008148 | 1/2003 |
| WO | WO 92/04072 | 3/1992 | | WO | WO 2004/012804 | 2/2004 |
| WO | 9207619 | 5/1992 | | WO | WO 2004/047899 | 6/2004 |
| WO | 9304722 | 3/1993 | | | | |
| WO | WO 93/11313 | 6/1993 | | * cited by examiner | | |

MEDICAL DEVICE WITH PUSH FORCE LIMITER

FIELD OF THE INVENTION

The invention pertains to medical devices and, more particularly, to medical devices, such as guidewires, catheters, or the like, having improved flexibility characteristics.

BACKGROUND

A wide variety of medical devices have been developed for medical use, for example, intravascular use. Some of these devices include guidewires or catheters that have certain flexibility characteristics. Of the known medical devices that have defined flexibility characteristics, each has certain advantages and disadvantages. There is an ongoing need to provide alternative designs and methods of making and using medical devices with desirable flexibility characteristics.

BRIEF SUMMARY

The invention provides design, material, and manufacturing method alternatives for medical devices having certain flexibility characteristics. In at least some embodiments, the medical devices include an elongate shaft that has a proximal portion, a distal portion, and an intermediate portion disposed between the proximal and distal portions that includes a region having a flexibility that is greater than that of the distal portion or the proximal portion.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings illustrate example embodiments of the claimed invention.

A number of different medical devices, for example guidewires, catheters, and the like, are used in certain medical procedures and for treating many types of disease. For example, an intravascular device can be inserted into the vascular system of the patient and navigated through the vasculature to a desired target site. Using this method, virtually any target site in the patient's vascular system may be accessed, including, for example, the coronary, cerebral, and peripheral vasculature.

When in use, such a medical device enters the patient's anatomy at a predetermined location and then is advanced toward a target region. While advancing the device a clinician may urge the distal tip forward by applying longitudinal forces to the proximal portion of the device. For the device to effectively communicate these longitudinal forces, it is desirable that the device have a high level of pushability or stiffness, particularly near the proximal end. Moreover, the path taken by a device within the anatomy may be tortuous, requiring the device to change direction frequently. In order for the device to navigate the tortuous anatomy, it is desirable for it to have certain flexibility characteristics, particularly near the distal end. The need for this combination of performance features is often addressed by manufacturing a medical device that has two or more discrete regions having different performance characteristics. For example, a relatively flexible distal section may be connected to a relatively rigid proximal section.

In some instances, the anatomy that the medical device is being advanced through may be partially or completely occluded. A number of complications could occur if the medical device encounters a partial or total occlusion. For example, the flexible distal tip could deflect and, possibly, damage or perforate a blood vessel or other anatomy through which it is navigating. In at least some embodiments, the invention includes a medical device with improved flexibility characteristics. For example, the device may include an increased flexibility portion located proximally of the distal tip that may act as a push force limiting structure, as described in more detail below.

Figure 1:
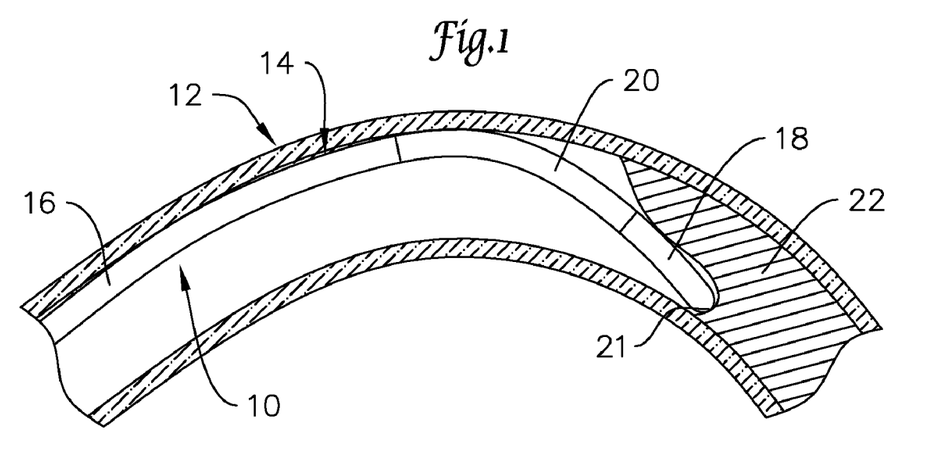
FIG. 1 is partial cross-sectional plan view of an example medical device disposed within a blood vessel.
Figure 2A:
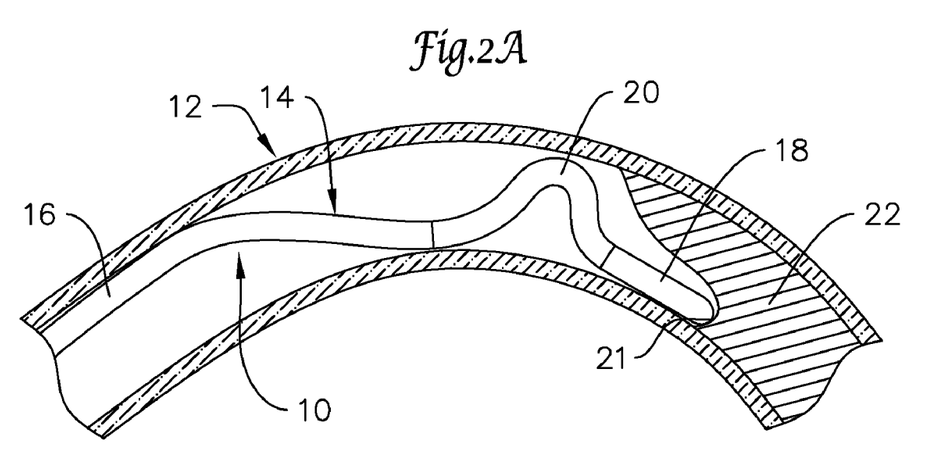
FIG. 2A is another partial cross-sectional view of an example medical device disposed within a blood vessel.
Figure 2B:
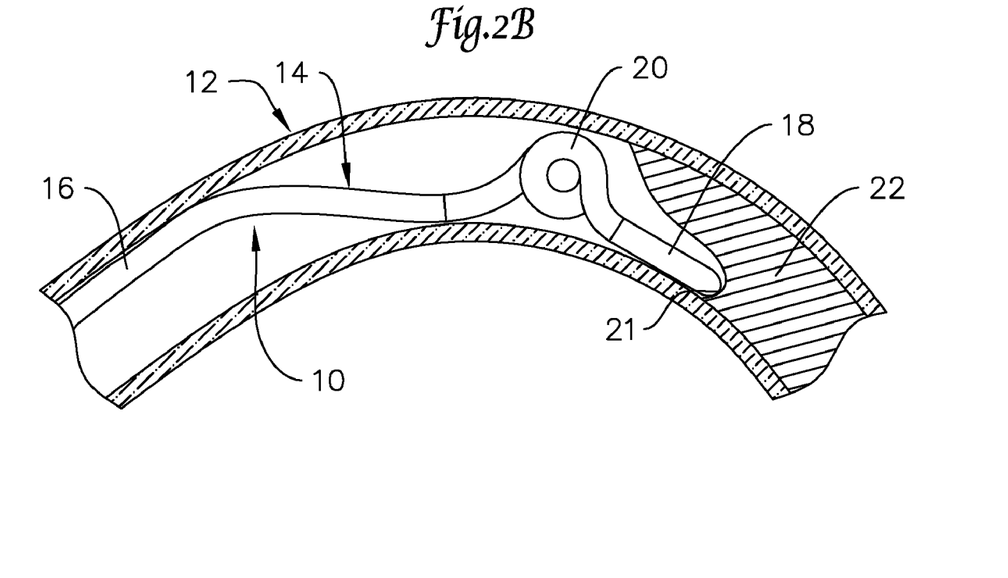
FIG. 2B is a partial cross-sectional view of another example medical device disposed within a blood vessel.
Figure 2C:
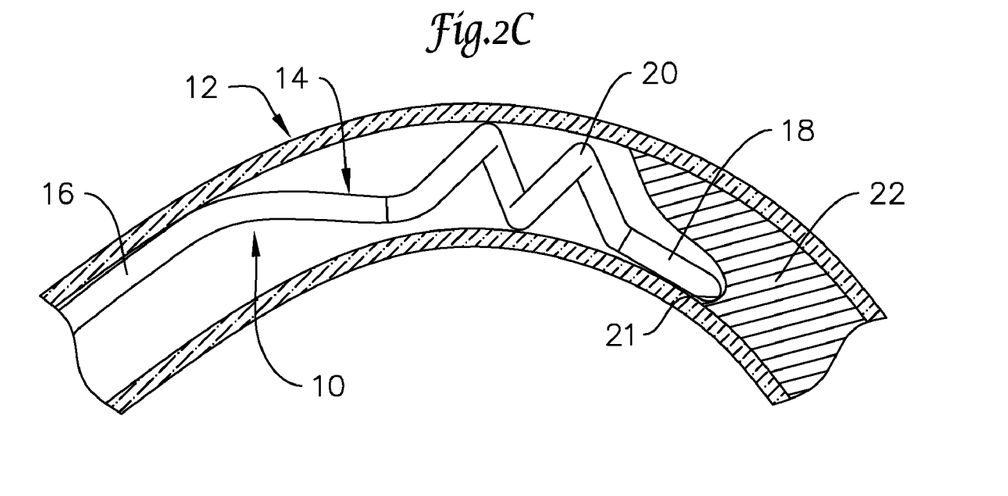
FIG. 2C is a partial cross-sectional view of another example medical device disposed within a blood vessel.

FIG. 1 shows an example medical device 10 disposed in a blood vessel 12. Device 10 includes an elongate shaft 14 having a proximal portion 16, a distal tip portion 18, and an intermediate portion 20. In general, device 10 is configured so that it can change shape, buckle, or otherwise alter in position or configuration, for example adjacent intermediate portion 20, if device 10 encounters a barrier or occlusion 22 as shown in FIG. 2A. Although the embodiments shown in FIGS. 1 and 2A depict device 10 simply as a shaft, it can be appreciated that these figures are illustrative in nature and that device 10 could be essentially any medical device or be any device designed to pass through an opening or body lumen. For example, device 10 may comprise a core wire (for use alone or with a variety of other medical devices), guidewire, catheter (e.g., therapeutic, diagnostic, or guide catheter), endoscopic device, laproscopic device, an embolic protection device, or any other suitable device. FIG. 2B illustrates another example medical device where the intermediate portion 20 may be configured to collapse into a loop upon buckling. FIG. 2C illustrates another example medical device where the intermediate portion 20 may be configured to collapse into a helical configuration upon buckling.

Intermediate portion 20 generally provides device 10 with a region having a decreased column strength or increased flexibility than the column strength or flexibility at a distal end 21 of device 10. Although the individual portions of device 10 have been called out as the proximal 16, distal 18, and intermediate portions 20, it can be appreciated that these names are not intended to limit the precise position of intermediate portion 20. For example, in at least some embodiments device 10 may include a generally stiff proximal portion 16 and a generally flexible distal portion 18. Additionally, the stiffness of proximal and distal portion 16/18 may vary along the length. Intermediate portion 20 can then be placed at essentially any position along the length of shaft 14. For example, intermediate portion 20 may be disposed between proximal and distal portion 16/18, within a region of proximal portion 16, within a region of distal portion 18, or even distally of distal portion 18. Because intermediate portion 20 generally provides a point of increased flexibility relative to the distal end of shaft 14, the later embodiment of device 10 would include a tip portion extending distally of intermediate portion 20 and distal portion 18.

Figure 3:
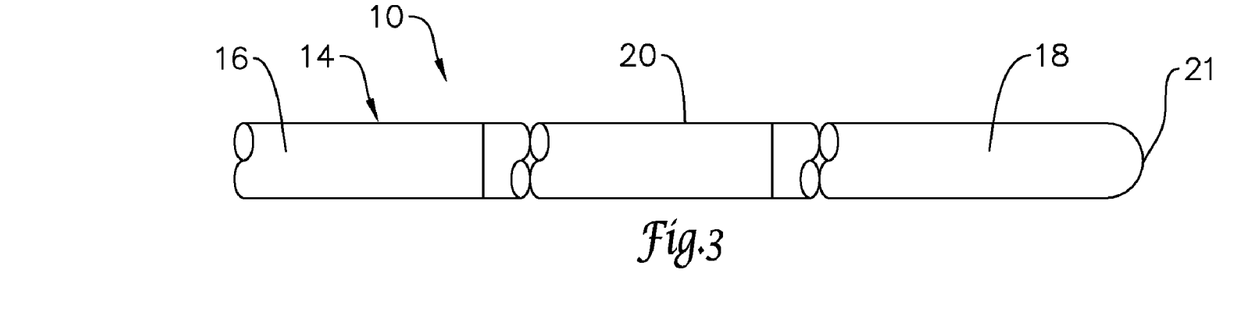
FIG. 3 is a plan overview of an example medical device.

FIG. 3 illustrates a plan overview of an example device 10. In some embodiments, device 10 is configured so that at least a part of intermediate portion 20 is disposed between a generally stiff proximal portion 16 and a generally flexible distal tip 18. According to this embodiment, distal tip 18 is more flexible than proximal portion 16, and at least a part of intermediate portion 20 is more flexible than distal tip 18. This feature allows device 10 to buckle at intermediate portion 20 if distal tip 18 is stopped, for example by an occlusion.

Buckling is generally understood to be a change in shape of device 10 that results in at least some lateral displacement of at least a portion of intermediate portion 20 that diverts force away from or prevents force from being transmitted to distal tip 18. Diverting or preventing the transmission of force to distal tip 18 can result in a reduced or nominal amount of displacement of distal tip 18. Thus, as force is applied to proximal portion of 16 in the distal direction, device 10 advances distally. When distal tip 18 encounters a barrier, additional distal force is diverted from distal tip 18 by the buckling of intermediate portion 20. As such, intermediate portion 20 acts as a push force limiter by limiting the amount of force that can be transmitted from proximal portion 16 to distal tip 18.

The buckling feature of device 10 can be achieved at or adjacent intermediate portion 20 by utilizing a number a different strategies. In some embodiments, the materials used to manufacture device 10 can be chosen so that intermediate portion 20 includes the desired buckling feature. For example, the different portions of shaft 14 can be made of any suitable materials including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Some examples of suitable polymers may include PTFE, fluorinated ethylene propylene (FEP), polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, linear low density polyethylene (for example REXELL®), polyetheretherketone (PEEK), polyimide (PI), polyetherimide (PEI), other suitable materials, or mixtures, combinations, or copolymers thereof. In some embodiments intermediate portion 20 can include a liquid crystal polymer (LCP) blended with other polymers to enhance torqueability.

In general, the materials used to construct device 10 can be chosen so that proximal portion 16 can be relatively stiff for pushability and torqueability, and distal portion 18 can be relatively flexible by comparison for better lateral trackability and steerability. For example, proximal portion 16 can be formed of straightened 304v stainless steel wire or ribbon, and distal portion 18 can be formed of a straightened super elastic or linear elastic alloy, for example a nickel-titanium alloy wire or ribbon. The materials used to construct intermediate portion 20 can then be chosen relative to those chosen for portions 16/18 in order to impart the desired push force limiting effect. For example, intermediate portion 20 can be manufactured from a metal, metal alloy, or polymer that is more flexible than the material used to construct distal tip 18. For example, in some example embodiments, proximal portion 16 can be constructed of rigid stainless steel, distal portion 18 can be nickel-titanium alloy, and intermediate portion 20 can be nickel-titanium alloy having more flexibility and less column strength than distal portion 18. Alternatively, all of shaft 14, or the distal and intermediate portions 18, 20 may be constructed from a single material, and be configured so that intermediate portion 20 has more flexibility and less column strength than distal portion 18. For example, all of shaft 14, or the distal and intermediate portions 18, 20 may be constructed from a nickel-titanium alloy, and be configured so that intermediate portion 20 has more flexibility and less column strength than distal portion 18.

The desired results can be achieved by employing selection of materials, processing, and/or structural techniques. More particularly, the use of different materials different processing techniques, different structure, or a combination of all of these allows different embodiments of intermediate portion 20 to be more flexible than the distal portion 18.

In some embodiments, the intermediate portion 20 can be engineered to buckle at a predetermined force and/or be tuned to buckle at a specific force. Thus, in embodiments where device 10 is a guidewire being advanced toward a total occlusion, it may be desirable to manufacture or configure intermediate portion 20 so that it will buckle before the pushing forces become high enough that distal tip 18 could displace and perforate, for example, a blood vessel.

In some embodiments, the materials, geometry, mechanical workings, structure, etc. can be used to design the push force limiting intermediate portion 20 to buckle at a specific predetermined force, thereby preventing additional force from being transmitted to the tip. In some embodiments, the amount of force at which point intermediate portion 20 will buckle can be in the range of about 0.01 Newtons to about 2.2 Newtons, or in the range of about 0.02 pound to about 0.5 pound.

Variations in materials, geometries, mechanical workings, etc. can also result in the shape or direction of the "buckle" to vary. For example, some configurations of intermediate portion 20 result in a generally lateral deflection when buckling. Alternatively, other embodiments include intermediate portion 20 being configured to buckle in a generally spiraling, looping, or helical manner. This configuration may allow intermediate portion 20 (and/or the buckled portion thereof) to buckle over a larger longitudinal distance and a smaller lateral distance. This feature may be desirable, for example, when device 10 is being used in relatively small or stenotic vessels.

In some embodiments, a coating, for example a lubricious, a hydrophilic, a protective, or other type of coating may be applied over portions or all or portions of device 10. Hydrophobic coatings such as fluoropolymers provide a dry lubricity which can improve guidewire handling and device exchanges. Lubricious coatings can also improve steerability and lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

In at least some embodiments, portions or all of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. For example, intermediate portion 20 may include radiopaque materials so that the clinician can monitor for the presence of any buckling. Some examples of radiopaque materials can include, but are not limited to, gold, platinum, palladium, tantalum, tungsten alloy, polymer material loaded with a radiopaque filler, and the like.

The different portions of device 10 can be connected using any suitable connecting technique such as welding, soldering, brazing, adhesive, mechanical interlocking, or the like, or combinations thereof. In some embodiments, the different portions of device 10 may be integral with one another or generally made of the same material but structurally different from one another. Alternatively, some embodiments can include one or more mechanical connectors or connector assemblies to connect the different portions of the core wire that are made of different materials. The connector may include any structure generally suitable for connecting portions of a guidewire. One example of a suitable structure includes a structure such as a hypotube or a coiled wire which has an inside diameter sized appropriately to receive and connect to the ends of proximal portion 16 and distal portion 18. Some other examples of suitable techniques and structures that can be used to interconnect different shaft sections are disclosed in U.S. Pat. No. 6,918,882, which is incorporated herein by reference.

The length of device 10, or the length of individual portions thereof, are typically dictated by the length and flexibility characteristics desired in the final medical device. In some example embodiments, proximal portion 16 may have a length in the range of about 20 to about 300 centimeters or more and distal portion 18 may have a length in the range of about 3 to about 50 centimeters or more. In some embodiments, the length of intermediate portion 20 may be in the range of about 5 centimeter or less, for example about 1 centimeter or less. It can be appreciated that alterations in the length of portions 16/18/20 can be made without departing from the spirit of the invention.

In addition, shaft 14 can have a solid cross-section, but in some embodiments, can have a hollow cross-section. In yet other embodiments, shaft 14 can include a combination of areas having solid cross-sections and hollow cross sections. Moreover, shaft 14, or portions thereof, can be made of rounded wire, flattened ribbon, or other such structures having various cross-sectional geometries. The cross sectional geometries along the length of shaft 14 can also be constant or can vary.

Figure 4:
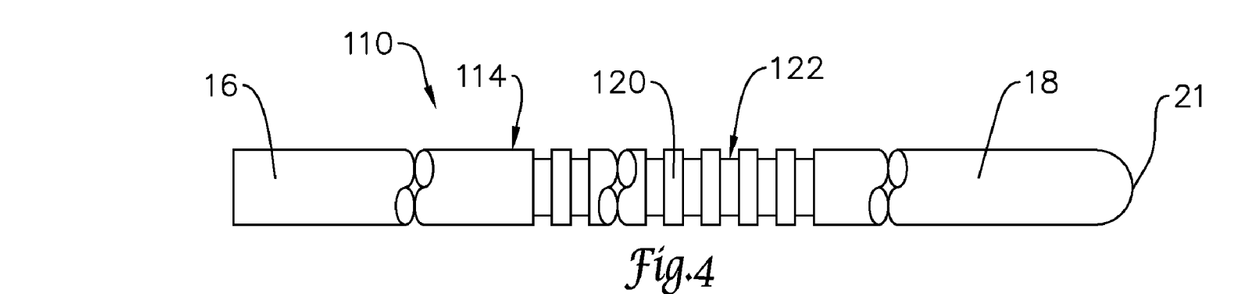
FIG. 4 is a partial cross-sectional view of an example medical device.

In some other embodiments, for example, with reference to FIG. 4, device 110 may include mechanical alterations in order to achieve the desired buckling feature. Device 110 is similar to device 10, shown in FIGS. 1-3, except that shaft 114 includes intermediate portion 120 having one or more cuts or notches 122 formed therein. Notches 122 can decrease the column strength and/or increase the flexibility of intermediate portion 120 so that at least a portion thereof can buckle if distal tip 21 encounters, for example, an occlusion.

Notches 122 may also allow intermediate potion 120 to be manufactured from the same material or from materials having a similar flexibility as proximal portion 16 and/or distal tip 20. For example, distal tip 21 may include linear-elastic or super-elastic nickel-titanium alloy and intermediate portion 120 may be defined by a region of the nickel-titanium alloy that includes notches 122. Similarly, proximal portion 16 may be comprised of a metal (e.g., stainless steel, nickel-titanium alloy, and the like including those described herein) and intermediate portion 120 may be defined by a region that includes notches 122. Although notches 122 are depicted as being squared in shape in FIG. 4, it can be appreciated that the shape, arrangement, and/or configuration of notches 122 can be altered without departing from the spirit of the invention. For example, notches may be rounded in shape, pointed in shape, have a "regular" or "irregular" configuration, spiral about intermediate portion 120, combinations of different shapes and configurations, and the like. Moreover, additional or alternative geometric alterations can be included such as twisting all or a part of intermediate portion 120 as well as any intermediate portion described herein.

Figure 5:
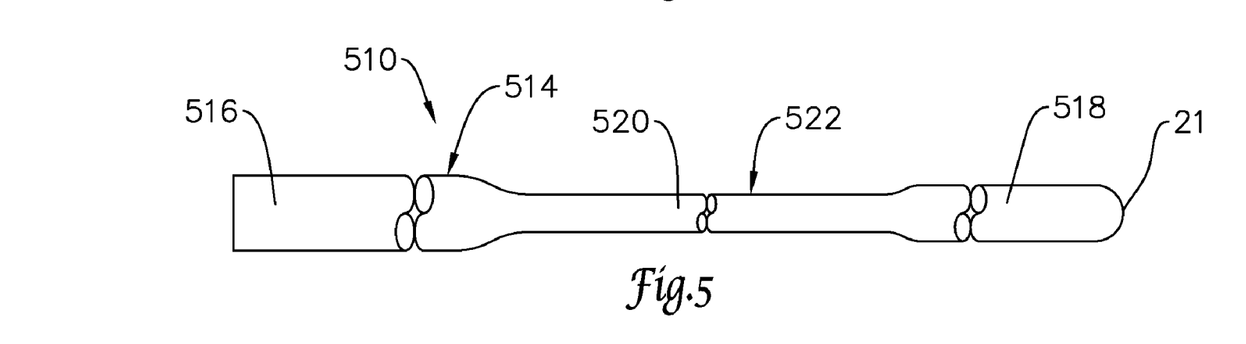
FIG. 5 is a partial cross-sectional view of another example medical device.

The number of notches 122 may also vary and include numbers between one and any other appropriate number. For example, FIG. 5 illustrates another example device 510 that is similar to device 110 except that shaft 514 includes intermediate portion 520 having one notch or necked region 522. According to this embodiment, push force limiting intermediate portion 520 may be defined by a narrowing in shaft 514. This structural feature can allow device 510 to be manufactured from one material while still having the desired push force limiting structural feature. It can be appreciated, however, that any of the materials described herein may be used to manufacture device 510, shaft 514, and any of the portions of shaft 514. Additionally, it may be desirable for distal portion 518 to be somewhat narrower or smaller in diameter than proximal portion 516. This feature can help impart distal flexibility to device 510, which may be desirable.

Figure 6:
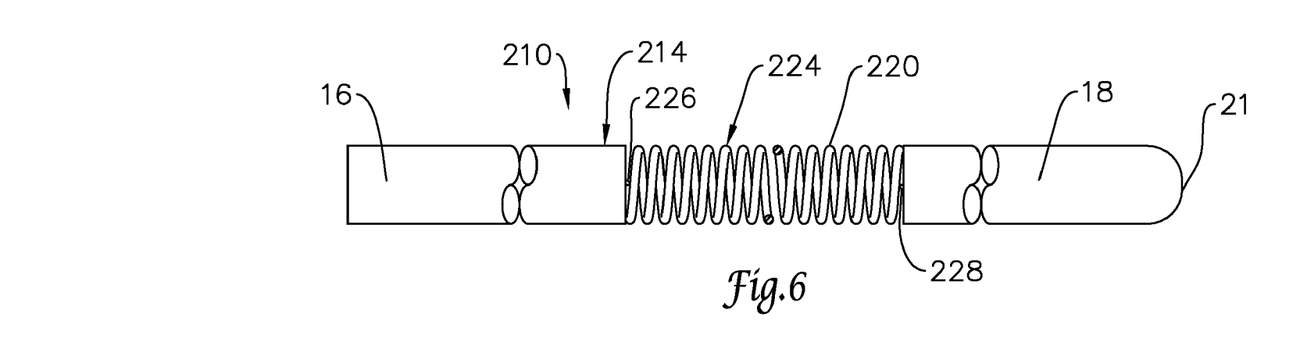
FIG. 6 is a partial cross-sectional view of another example medical device.

Another example medical device 210 is shown in FIG. 6. Device 210 is similar to devices 10/110, as in FIG. 1-5, except that intermediate portion 220 of shaft 214 includes a coil or coiled region 224. Coil 224 may be generally positioned at intermediate region 220. In some embodiments, coil 224 may be disposed over a core member (not shown) or other suitable support structure. Alternatively, the inner cavity defined by coil 224 may be substantially hollow.

Coil 224 can be manufactured from a number of suitable materials, including, for example, metals, metal alloys, polymers, metal-polymer composites, and the like. Some examples of materials include stainless steel, nickel-chromium alloy, nickel-chromium-iron alloy, cobalt alloy, platinum, or other suitable materials, and the like. Some additional examples of suitable material include straightened super elastic or linear elastic alloy (e.g., nickel-titanium) wire, or alternatively, a polymer material, such as a high performance polymer. In some embodiments, coil 224 can be made of ,in full or in part, coated with, or doped with a radiopaque material.

Coil 224 may be formed of round wire or flat ribbon ranging in dimensions to achieve the desired characteristics, such as flexibility, and be wrapped in a generally helical fashion by conventional winding techniques. The pitch of adjacent turns of coil 224 may be tightly wrapped so that each turn touches the succeeding turn or the pitch may be set such that coil 224 is wrapped in an open fashion. Moreover, the pitch of the coil can be varied along the length device 210. In some embodiments, a coating, for example a lubricious (e.g., hydrophylic) or other type of coating may be applied over portions or all of coil 224. Some examples of such coatings include those discussed above. Additionally, the thickness of coil 224 may be varied along the longitudinal axis of the device 210.

Coil 224 may include a proximal end 226 that is coupled to or otherwise attached to proximal portion 16. Coil 224 can be attached using suitable attachment mechanism, for example a solder joint or other suitable attachment means such as adhesive, thermal bonding, mechanical bonding, and the like. A distal end 228 of coil 224 may be coupled to distal tip portion 18, for example, analogously to how proximal end 226 is coupled to proximal portion 16 or by any other suitable connection.

Figure 7:
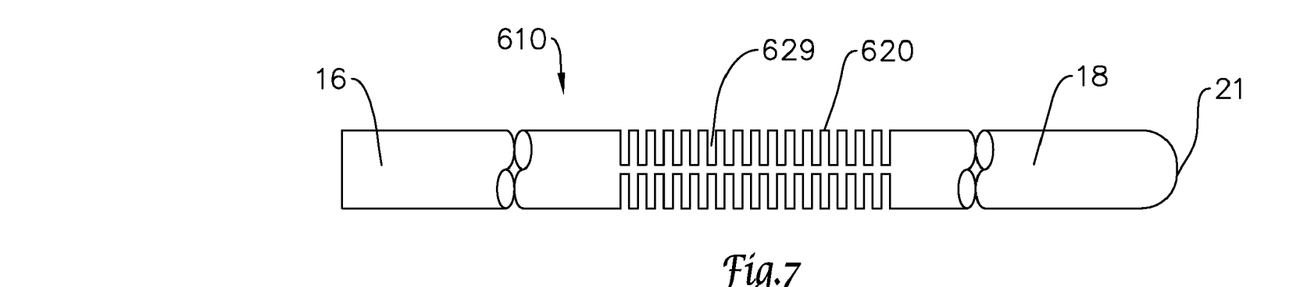
FIG. 7 is a partial cross-sectional view of another example medical device.

Another example medical device 610 is shown in FIG. 7. This device is similar to the other devices described herein except that intermediate region 620 includes a plurality of slots 629 formed or cut therein. Slots 629 can decrease the column strength and/or flexibility of intermediate portion 620 so that at least a portion thereof can buckle if distal tip 21 encounters, for example, an occlusion. The material composition may vary to include any of the materials described herein. For example, intermediate region 620 may include stainless steel and/or may be a stainless steel hypotube that includes slots 629. Additionally, the number of slots 629, the length of intermediate portion 620, and other characteristics of device 610 may vary in a manner analogous to what is described in relation to any of the other example embodiments.

Figure 8:
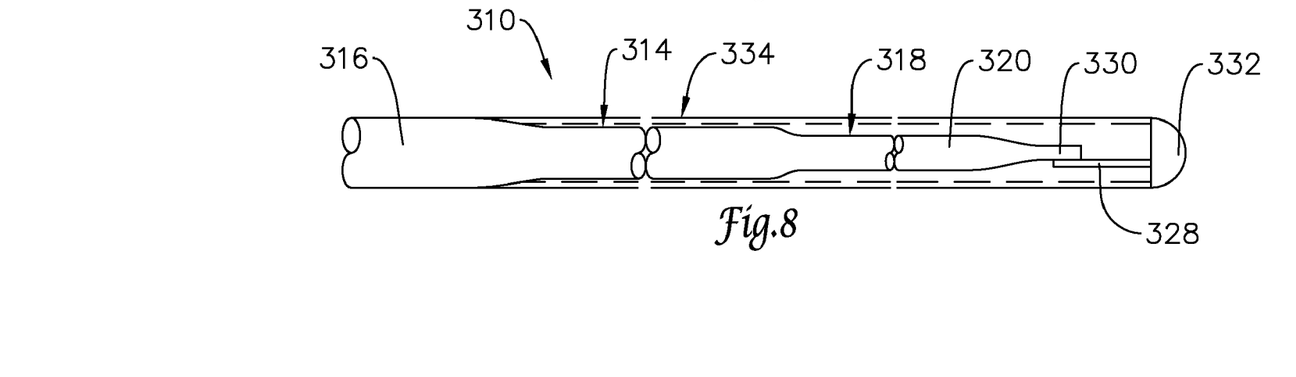
FIG. 8 is a partial cross-sectional view of another example medical device.

Medical devices including such push force limiting structure can also include additional structure. For example, such structures as a coil, a sheath, a shaping ribbon, a marker member, a solder tip, or the like can be present on the device, for example, near the distal end, or on other portions of the device. For example, FIG. 8 is a partial cross-sectional view of another example medical device 310, which in this example is a guidewire. Device 310 includes a shaft 314 having a proximal portion 316 and a distal portion 318. According to this embodiment, shaft 314 may be a core wire. Proximal portion 316 is similar to proximal portion 16 above. Distal portion 318 is similar to distal tip portion 18, except that it includes a push-force limiting intermediate portion 320. Intermediate portion 320 can take the form of any of the aforementioned intermediate portions (20, 120, 220, and variants thereof). Device 310 may also include a distal shaping ribbon 328 that may extend, for example, from the distal end 330 of distal portion 318 to a distal solder ball tip 332 and an outer member or sheath 334 disposed over at least a portion of device 310, for example over distal portion 318.

In at least some embodiments, intermediate portion 320 is located a distance away from a distal end 330 of distal portion 318. For example, distal portion may have a length of about 1-300 centimeters or longer and intermediate portion 320 may be located about 1-50 centimeters from distal end 330. Moreover, the length, shape, materials, configuration, etc. of intermediate portion may be substantially similar to the example embodiments of intermediate portions 20/120/220 described above. For example, the materials used to manufacture intermediate portion 320 may include a polymer, metal, or any other material including those described herein that has a flexibility that is greater than the material found at regions of distal portion 318 that are located distally of intermediate portion 320.

As shown in FIG. 8, distal portion 318 of shaft 314 may include one or more tapered regions. In some embodiments the distal portion 318 may be tapered and have an initial outside size or diameter that can be substantially the same as the outside diameter of proximal portion 316, which then tapers to a reduced size or diameter. For example, in some embodiments, distal portion 318 can have an initial outside diameter that is in the range of about 0.010 to about 0.020 inches, that tapers to a diameter in the range of about 0.001 to about 0.005 inches. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. Although FIG. 8 depicts distal portion 318 of shaft 314 as being tapered, it can be appreciated that essentially any portion of shaft 314 may be tapered and the taper can be in either the proximal or the distal direction. As shown in FIG. 8, the tapered region may include one or more portions where the outside diameter is narrowing, for example, the tapered portions, and portions where the outside diameter remains essentially constant, for example, constant diameter portions. The number, arrangement, size, and length of the narrowing and constant diameter portions can be varied to achieve the desired characteristics, such as flexibility and torque transmission characteristics. The narrowing and constant diameter portions as shown in FIG. 8 are not intended to be limiting, and alterations of this arrangement can be made without departing from the spirit of the invention.

The tapered and constant diameter portions of tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing shaft 314 during the grinding process. In some embodiments, shaft 314 is centerless ground using a Royal Master HI-AC centerless grinder.

The cross-sectional shape of shaft 314 may also vary. For example, FIG. 8 depicts shaft 314 as having a round cross-sectional shape. It can be appreciated that other cross-sectional shapes or combinations of shapes may be utilized without departing from the spirit of the invention. For example, the cross-sectional shape of shaft 314 may be oval, rectangular, square, polygonal, and the like, or any suitable shape.

Sheath 334 may be manufactured from a suitable material such as a metal or metal alloy, a polymer, a metal-polymer composite, and the like including any of those listed above. In some embodiments, sheath 334 may be multi-layer (indicated in FIG. 8 by phantom lines). For example, sheath 334 include a first layer disposed generally over distal portion 318 and a second layer disposed over the first layer. One or more of the layers may be coated with, doped, or otherwise include a radiopaque material, including any of those listed above. For example, the second layer may comprise an outer radiopaque jacket. Sheath 334 may also take a number of different forms. For example, sheath 334 may comprise a solid structure wherein distal portion 318 is essentially embedded. Alternatively, sheath 334 may be substantially tubular so that a space may be present between at least some regions of distal portion 318 and sheath 334.

Figure 9:
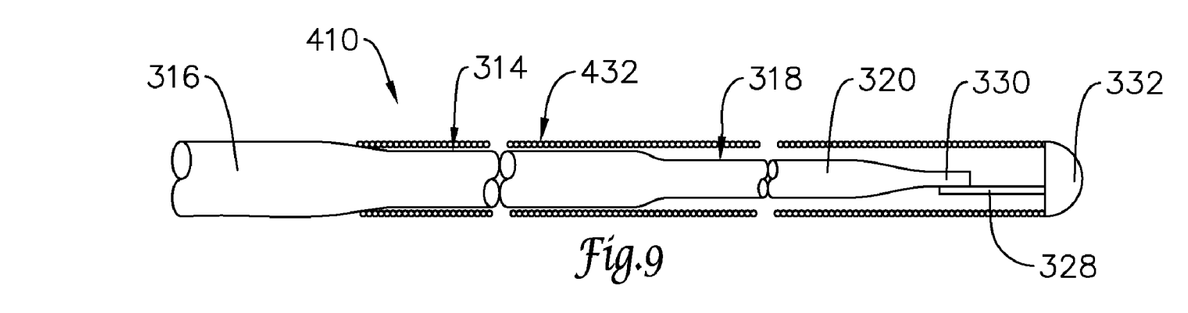
FIG. 9 is a partial cross-sectional view of another example medical device.

Another example medical device 410 is illustrated in FIG. 9. Device 410 is similar to device 310 except that outer member 432 may include a coil. It can be appreciated that any of the alternatives described in relation to coil 224 above are available to outer member 432. For example, it is within the spirit of the invention that outer member 432 may have a number of different material compositions (including metal, metal alloys, polymers, and the like), differences in pitch, differences in length, and the like. Moreover, outer member 432 may be configured so that is tightly associated or attached with distal portion 318 or outer member 432 may be spaced a distance away from regions of distal portion 318.

Figure 10:
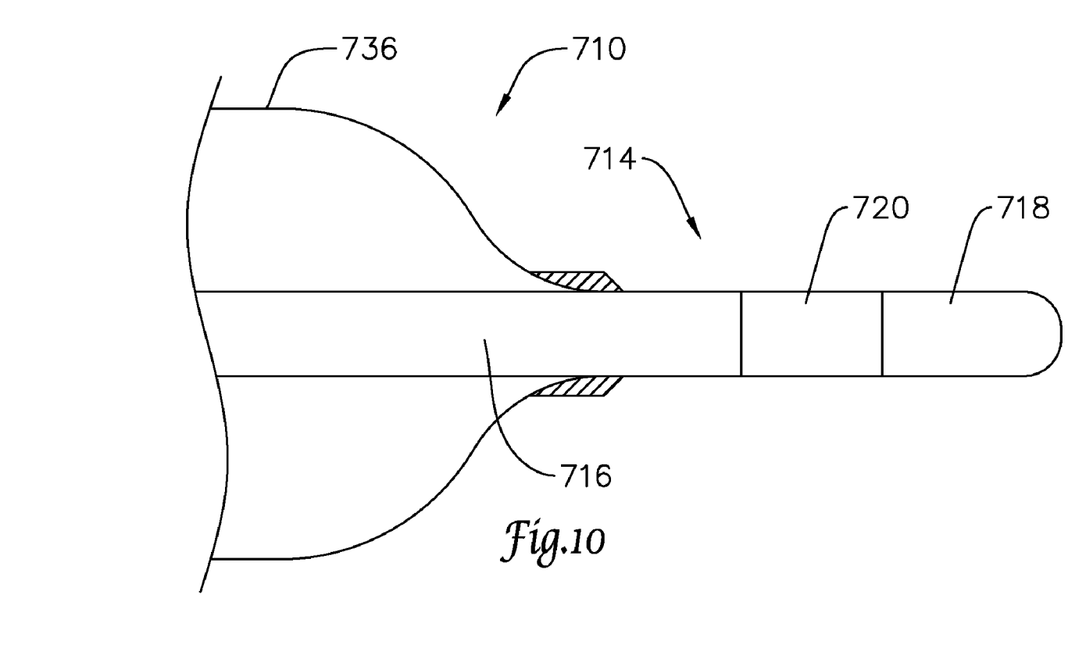
FIG. 10 is a partial cross-sectional view of another example medical device.

Another example medical device 710 is illustrated in FIG. 10. Device 710 may comprise a fixed wire device, similar to those known in the art, in order to illustrate that the desirable features and characteristics may be useful in fixed wire devices. Device 710, which is otherwise similar to other devices described herein, is illustrated in FIG. 10 as being a fixed wire balloon catheter including an expandable balloon 736 and shaft 714. Shaft 714 may include proximal region 716, distal region 718, and intermediate region 720. Intermediate region 720 may similar to any of the other intermediate regions described herein so that it may buckle and/or function as a push-force limiter.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
   a core wire having a distal tip, a proximal portion having a distal end, a distal portion having a proximal end, and an intermediate portion having a proximal and a distal end, the distal portion including the distal tip and extending from the distal tip to the distal end of the intermediate portion, the intermediate portion extending from the proximal end of the distal portion to the distal end of the proximal portion; and
   an outer member disposed over the core wire and extending from the distal tip to the proximal portion, the outer member having a generally constant flexibility;
   wherein the intermediate portion of the core wire is more flexible than the distal portion of the core wire and the proximal portion of the core wire, and
   wherein the distal portion has a length from the proximal end to the distal tip that is greater than the maximum width of the distal portion; and
   wherein the intermediate portion is configured to buckle when subjected to a force equal to a preselected force in the range of about 0.02 pound to about 0.5 pound.

2. The medical device of claim 1, wherein the distal portion is more flexible than the proximal portion.

3. The medical device of claim 1, wherein the proximal portion comprises stainless steel.

4. The medical device of claim 1, wherein the distal portion comprises nickel-titanium alloy.

5. The medical device of claim 1, wherein the intermediate portion comprises a polymer.

6. The medical device of claim 1, wherein the intermediate portion includes an outer surface and one or more notches defined in the outer surface.

7. The medical device of claim 1, wherein the intermediate portion includes a coil.

8. The medical device of claim 1, wherein the outer member comprises a sheath disposed over at least a portion of the core wire.

9. The medical device of claim 8, wherein the sheath includes a radiopaque material.

10. The medical device of claim 1, wherein the outer member comprises a coil disposed over at least a portion of the core wire.

11. The medical device of claim 1, wherein the intermediate portion comprises a different material of construction than the proximal and distal portions.

12. The medical device of claim 1, wherein the intermediate portion has a cross-sectional area that is different than a cross-sectional area of both the proximal and distal portions.

13. The medical device of claim 12, wherein the intermediate portion has a smaller cross-sectional area than both the proximal and distal portions.

14. The medical device of claim 1, wherein the intermediate portion comprises a different material of construction than the proximal region and the distal tip.

15. The medical device of claim 1, wherein the intermediate portion has a cross-sectional area that is different than a cross-sectional area of both the proximal region and the distal tip.

16. The medical device of claim 15, wherein the intermediate portion has a smaller cross-sectional area than both the proximal region and the distal tip.

17. The medical device of claim 1 wherein the distal portion has a length between about 3 cm and about 50 cm.

18. The medical device of claim 17 wherein the distal portion has a length greater than about 10 cm.

19. The medical device of claim 1 wherein the core wire has a first state where the intermediate portion and the distal portion are generally free from load in an axial direction and are generally straight and wherein the guidewire has a second state under axial load where the distal portion is generally straight and the intermediate portion is buckled.

20. The medical device of claim 19 wherein in the second state the intermediate portion forms a generally U-shaped buckle.

21. The medical device of claim 19 wherein in the second state the intermediate portion buckling includes a generally lateral deflection.

22. The medical device of claim 19 wherein in the second state the intermediate portion buckles in a generally helical manner.

23. The medical device of claim 19 wherein in the second state the intermediate portion buckles in a generally looping manner.

24. The medical device of claim 23 wherein the distal tip has a maximum diameter of about 0.020 inches.

25. A guidewire, comprising:
an elongate core member having a proximal portion and a distal portion having a distal end;
a push-force limiter region having a distal end, the push-force limiter region coupled to the distal end of the distal portion;
a distal tip coupled to the distal end of the push-force limiter region;
wherein the distal portion is more flexible than the proximal portion;
wherein the distal tip is more flexible than the distal portion; and
wherein the push-force limiter region is more flexible than the distal tip, and
wherein the distal tip has a length along a longitudinal axis of the guidewire that is greater than its maximum width;
an outer member disposed over the elongate core member and extending from the distal end of the core member to the proximal portion of the core member, the outer member having a length along the longitudinal axis and a generally constant flexibility along its length; and
wherein the push-force limiter region is configured to buckle when subjected to a force equal to a preselected force in the range of about 0.02 pound to about 0.5 pound.

26. The guidewire of claim 25, wherein the distal portion includes one or more tapers.

27. The guidewire of claim 25, wherein the push-force limiter region includes an outer surface and one or more notches defined in the outer surface.

28. The guidewire of claim 25, wherein the push-force limiter region includes a coil.

29. The guidewire of claim 25, wherein the outer member comprises a sheath disposed over at least a portion of the core member.

30. The guidewire of claim 29, wherein the sheath includes a radiopaque material.

31. The guidewire of claim 29, wherein the sheath extends distally beyond the distal tip, and further comprising a distal shaping region coupled to and extending distally from the distal tip.

32. The guidewire of claim 25, wherein the outer member comprises a coil disposed over at least a portion of the core member.

33. The guidewire of claim 25, wherein the push-force limiter region comprises a different material of construction than the proximal portion and the distal portion.

34. The guidewire of claim 25, wherein the push-force limiter region has a cross-sectional area that is different than a cross-sectional area of both the proximal portion and the distal portion.

35. The guidewire of claim 34, wherein the push-force limiter region has a smaller cross-sectional area than both the proximal portion and the distal portion.

36. The guidewire of claim 25 wherein the distal tip has a length between about 1 cm and about 50 cm.

37. The guidewire of claim 25 wherein the guidewire has a first state where the push-force limiter region and the distal tip are generally free from load in an axial direction and are generally straight and wherein the guidewire has a second state under axial load where the distal tip is generally straight and the push-force limiter region is buckled.

* * * * *